United States Patent [19]
Takezawa et al.

[11] Patent Number: 6,061,139
[45] Date of Patent: May 9, 2000

[54] NONDESTRUCTIVE DIAGNOSTIC METHOD AND NONDESTRUCTIVE DIAGNOSTIC APPARATUS

[75] Inventors: Yoshitaka Takezawa, Hitachinaka; Yoshikiyo Kashiwamura, Hitachi; Ikushi Kano, Tokai-mura, all of Japan

[73] Assignee: Hitachi, Ltd, Tokyo, Japan

[21] Appl. No.: 08/943,230

[22] Filed: Oct. 3, 1997

[30] Foreign Application Priority Data

Oct. 4, 1996 [JP] Japan .................................. 8-264038

[51] Int. Cl.$^7$ .................................................. G01N 21/25
[52] U.S. Cl. .......................... 356/407; 356/70; 356/382; 356/434
[58] Field of Search ............................. 356/70, 382, 407, 356/408, 425, 434

[56] References Cited

U.S. PATENT DOCUMENTS 5,049,742   9/1991   Hosonuma et al. ...................... 356/70

*Primary Examiner*—Richard A. Rosenberger
*Attorney, Agent, or Firm*—Antonelli, Terry, Stout & Kraus, LLP

[57] ABSTRACT

To nondestructively diagnose a weight reduction ratio of an insulating material or a lubricating oil without stopping operation of the equipment, a nondestructive diagnostic method uses an optical fiber probe type sensor in which a light transmission loss or a reflective absorbance difference is used as a parameter.

17 Claims, 4 Drawing Sheets

NONDESTRUCTIVE DIAGNOSTIC METHOD AND NONDESTRUCTIVE DIAGNOSTIC APPARATUS

BACKGROUND OF THE INVENTION

The present invention relates to a nondestructive diagnostic method and apparatus which can nondestructively and optically diagnose the weight reduction ratio of an insulating material, a structural material, a lubricating oil or the like, which is used in equipment, irrespective of whether it is a liquid or solid, without stopping the operation of the equipment.

As a nondestructive diagnostic apparatus for evaluating the degree of deterioration of an insulating material in a rotating machine, Japanese Patent Laid-Open Publication No. Sho 64-84162 discloses a diagnostic apparatus in which an irradiated light beam supplied from a white standard light source and directed by an optical fiber is reflected by a sensor unit made of a material which is the same as the insulating material. The reflected light beam is detected via a light receiving optical fiber, and a color specification arithmetic operation is executed by using chromaticity or a difference in chromaticity, based on the L*a*b* color specification system. L* is a lightness index showing lightness and a* and b* are called chromatic indices showing chromaticity (hue and saturation).

According to the conventional technique mentioned above, when equipment, such as a rotating machine, is produced, it is necessary to preliminarily embed the irradiation optical fiber, the light receiving optical fiber, and the sensor unit in an insulating layer of the equipment. There is, consequently, a substantial problem in that the above technique cannot be applied to existing equipment in which those optical fibers and the sensor are not already embedded in the machine.

Further, the conventional technique cannot diagnose the weight reduction ratio of a material.

SUMMARY OF THE INVENTION

An object of the present invention is to provide a nondestructive diagnostic method and apparatus which can solve the above problems and which can optically and nondestructively diagnose the weight reduction ratio of an insulating material or a structural material which is used for equipment, irrespective of whether it is a liquid or solid, without stopping the operation of the equipment.

The inventors of the present invention have examined the relation between reduction in weight of a resin or oil and the optical physical properties thereof, and they have found that the nondestructive diagnostic method and the nondestructive diagnostic apparatus of the invention can accurately determine the weight reduction ratio from a change in the intensity of the light beam reflected by the surface of the resin or oil or the intensity of a transmitted light beam in association with thermal deterioration. That is, the gist of the invention is as follows.

(1) A nondestructive diagnostic method comprising the steps of: directing irradiation light beams from at least two kinds of monochromatic light sources at different wavelengths and irradiating the light beams onto a surface of an object to be measured using an irradiation optical fiber; leading the reflected light beams from the surface of the object to be measured to a detector by using a light receiving optical fiber; calculating a reflective absorbance ($A\lambda$) at each wavelength by using the following expression (1) from an output of the detector, and after that, calculating a reflective absorbance difference ($\Delta A\lambda$) at the different wavelengths by using the following expression (2), and further comparing preliminarily stored values of weight reduction ratio of the object to be measured with the reflective absorbance difference at the different wavelengths, thereby determining the weight reduction ratio of the object to be measured in a data processing unit.

$$A\lambda = -log(R\lambda/100) \quad (1)$$

$$\Delta A\lambda = A\lambda 1 - A\lambda 2 \, (where \, \lambda 1 < \lambda 2) \quad (2)$$

The reflectance of the object to be measured at a wavelength of $\lambda$ (nm) is set to $R\lambda$ (%).

(2) A nondestructive diagnostic apparatus comprising: at least two kinds of monochromatic light sources producing light at different wavelengths; an optical coupler for leading light beams from the light sources to an irradiation optical fiber for irradiating the light beams from the light sources onto a surface of an object to be measured; a light receiving optical fiber for receiving reflected light beams from the surface of the object to be measured and leading the received light beams to a detector for detecting the intensity of each of the reflected light beams at the different wavelengths and outputting measured values as electric signals to the outside; and a data processing unit for calculating a reflective absorbance ($A\lambda$) at each wavelength from an output value of the detector by using the following expression (1), calculating the reflective absorbance difference ($\Delta A\lambda$) at the different wavelengths by using the following expression (2), and further, comparing preliminarily stored values of weight reduction ratio of the object to be measured with the reflective absorbance difference at the different wavelengths, thereby determining the weight reduction ratio of the object to be measured.

$$A\lambda = -log(R\lambda/100) \quad (1)$$

$$\Delta A\lambda = A\lambda 1 - A\lambda 2 \, (where \, \lambda 1 < \lambda 2) \quad (2)$$

The reflectance of the object to be measured at the wavelength of $\lambda$ (nm) is set to $R\lambda$ (%).

(3) A nondestructive diagnostic method comprising the steps of: directing an illumination light beam from a light source of at least one kind of monochromatic light beam and irradiating the light beam onto an object to be measured having a thickness of t (mm) using an irradiation optical fiber; leading a transmitted light beam from the object to be measured to a detector by using a light receiving optical fiber which is arranged so as to face the irradiation optical fiber; calculating a light transmission loss ($L\lambda$, dB/mm) from an output of the detector by using the following expression (3), and comparing preliminarily stored values of weight reduction ratio of the object to be measured with the light transmission loss, thereby determining the weight reduction ratio of the object to be measured in a data processing unit.

$$L\lambda = (10/t) \times A\lambda \quad (3)$$

The absorbance of the object to be measured at the wavelength of $\lambda$ (nm) is set to $A\lambda$.

(4) A nondestructive diagnostic apparatus comprising: a light source of at least one kind of monochromatic light beam; an irradiation optical fiber for irradiating the light from the light source to an object to be measured having a thickness of t (mm); a light receiving optical fiber, which is arranged so as to face the optical fiber for irradiation, for receiving a transmitted light beam from the object to be measured and for leading the light beam to a detector for detecting the intensity of the transmitted light beam and outputting the measured value as an electric signal to the outside; and a data processing unit for calculating a light transmission loss ($L_1$, dB/mm) from an output value of the detector by using the following expression (3) and comparing preliminarily stored weight reduction ratio of the object to be measured with the light transmission loss, thereby determining the weight reduction ratio of the object to be measured.

$$L\lambda = (10/t) \times A\lambda \qquad (3)$$

The absorbance of the object to be measured at the wavelength of 1 (nm) is set to $A_1$.

(5) A nondestructive diagnostic method comprising the steps of: directing irradiated light beams from light sources of at least two kinds of monochromatic light beams having different wavelengths and irradiating the light beams onto a surface of an object to be measured using an irradiation optical fiber; leading reflected light beams from the surface of the object to be measured to a detector by using a light receiving optical fiber; and comparing a preliminarily stored value of weight reduction ratio of the object to be measured with the reflective absorbance difference at the different wavelengths, thereby determining the weight reduction ratio of the object to be measured in a data processing unit.

(6) A nondestructive diagnostic method comprising the steps of: leading and irradiating light beams from a tungsten halogen lamp, which irradiates white continuous light beams, onto a surface of an object to be measured using an irradiation optical fiber; leading reflected light beams from the surface of the object to be measured to a detector having a spectroscope by using a light receiving optical fiber; and comparing preliminarily stored values of weight reduction ratio with a reflective absorbance difference at different wavelengths, thereby determining the weight reduction ratio of the object to be measured in a data processing unit.

(7) A nondestructive diagnostic apparatus comprising: at least two kinds of monochromatic light sources producing light at different wavelengths; an optical coupler for leading light beams from the light sources to an irradiation optical fiber for irradiating the light beams from the light sources onto a surface of an object to be measured; a light receiving optical fiber for receiving reflected light beams from the surface of the object to be measured and leading the light beams to a detector for detecting the intensity of each of the reflected light beams at the different wavelengths and outputting measured values as electric signals to the outside; and a data processing unit for comparing a reflective absorbance at each wavelength with preliminarily stored values of weight reduction ratio of the object to be measured from an output value of the detector, thereby determining the weight reduction ratio of the object to be measured.

(8) A nondestructive diagnostic apparatus comprising: a light source in the form of a tungsten halogen lamp for irradiating white continuous light beams; an irradiation optical fiber for irradiating the light beams from the light source onto a surface of an object to be measured; a light receiving optical fiber for receiving reflected light beams from the surface of the object to be measured and leading the light beams to a detector having a spectroscope for detecting the intensity of each of the reflected light beams at the different wavelengths which are dispersed by the spectroscope and outputting measured values as electric signals to the outside; and a data processing unit for comparing a reflective absorbance difference at the different wavelengths with preliminarily stored values of weight reduction ratio of the object to be measured from output values of the detector, thereby determining the weight reduction ratio of the object to be measured.

As a monochromatic light source, a LED (a light emitting diode) and a LD (a laser diode) each emitting a light beam having a peak wavelength in a range from 660 to 1550 nm are preferable, since they can be easily obtained, they have a life which is long, and they provide a performance which is stable. Especially, LED and LD light sources emitting a light beam having a peak wavelength of 660, 670, 780, 800, 850, 1030, 1300, 1550 nm, or the like are preferred. With light sources emitting light beams at wavelengths outside of the above range, there is a possibility that a detector (photocell) cannot detect the light beams since they are out of range in a state where the weight reduction ratio of the object to be measured is still relatively small.

When the object to be measured is an acrylate resin, polycarbonate resin, mineral oil, or the like, which is originally very transparent, light beams at wavelengths of 660, 670, 780, 800, 850 nm, and the like are suitable. On the other hand, when the object to be measured is an alkyd resin or unsaturated polyester resin, which is originally colored, an epoxy resin which is immediately colored black, an opaque resin including a pigment or the like, light beams at wavelengths in a near infrared region of 780, 800, 850, 1030, 1300, 1550 nm and the like are suitable.

According to the present invention, since it is unnecessary to preliminarily embed an irradiation optical fiber and a light reception optical fiber in equipment, the optical fibers are not required to have a high heat resistance. Optical fibers made of plastic, each having a large diameter, can be used, which is advantageous in improving the light-intercepting efficiency.

The relation between the preliminarily stored values of weight reduction ratio of the object to be measured and the reflective absorbance difference at different wavelengths, or the relation between the weight reduction ratio of the object to be measured and a light transmission loss can be obtained by an accelerated deterioration test which is performed as a model. The obtained relation diagram is generally called a diagnostic master curve. FIGS. 3 and 4 show representative examples. The accelerated deterioration test is not especially limited, but can be performed by using a conventionally known technique.

A change in spectrum of the absorbance in association with thermal deterioration of an organic material is represented by a change as shown in FIG. 2. Since the reflective absorbance shows a remarkable increase on the shorter wavelength side in a visible range in association with deterioration as shown in the diagram, it is very difficult to keep on measuring the absorbance of a material which is being used until the end of the life of equipment in a range shorter than 660 nm due to the limited measurement range of the detector. The increase in the reflective absorbance on the shorter wavelength side is mainly due to an increase in electron transition absorption loss by a deterioration reaction of thermal oxidation of the material.

Since the absorbance increases toward the shorter wavelength side in association with advance in deterioration, the reflective absorbance difference $DA_1$ (=$Al_1-Al_2$) at two arbitrary wavelengths similarly increases. In this case, $1_1<1_2$. For example, in FIG. 2, when the reflective absorbance difference $DA_1$ at the wavelengths (nm) and $1_2$ (nm) is set to a1, a2, and a3 for a material in which deterioration is large, a material in which deterioration is small, and a material in an initial state, respectively, the relation of a1>a2>a3 is satisfied. A similar relation can be also obtained with respect to the light transmission loss.

As disclosed in Japanese Patent Laid-Open Publication No. Hei 3-226651, the degree of deterioration is expressed by reduced time θ. By expressing the reduced time q, even if materials having various thermal histories are used, if the reduced time q is the same, it denotes that the degree of deterioration is the same. The reduced time q (h) is defined by an expression (4).

$$\theta = \int_0^t exp(-\Delta E/RT) dt \tag{4}$$

where, DE is apparent activation energy (J/mol) of the thermal deterioration, R is a gas constant (J/K/mol), T an absolute value (K) of thermal deterioration, and t is deterioration time (h). The value DE of resin or oil can be easily calculated by Arrenius plotting the change in the reflective absorbance difference or the change in light transmission loss at a few kinds of deterioration temperatures.

When preliminarily obtained reduced time q at the end of life of the equipment using the resin, the oil, or the like is set to $q_0$, the difference $D_q(=q_0-q)$ between the reduced time $q_0$ and the actually obtained reduced time q is reduced time corresponding to the remaining life and is used as a scale to determine the degree of deterioration. That is, the remaining life $D_q$ (h) can be represented by expression (5).

$$\Delta\theta = \theta_0 - \theta = \int_0^{t0} exp(-\Delta E/RT) dt \tag{5}$$

When the operating temperature condition of the equipment after the time t is determined, the time of the remaining life Dt ($=t_0-t$) can be obtained according to the expression (5).

If the operating time t of actual equipment is known, the average temperature T when the equipment is used can be also estimated by using the expression (4). This will be described by reference to various embodiments in the more detailed description of the present invention.

DESCRIPTION OF THE PREFERRED EMBODIMENTS

The present invention will be described in detail hereinbelow by reference to various embodiments.
(First Embodiment)

Figure 1:
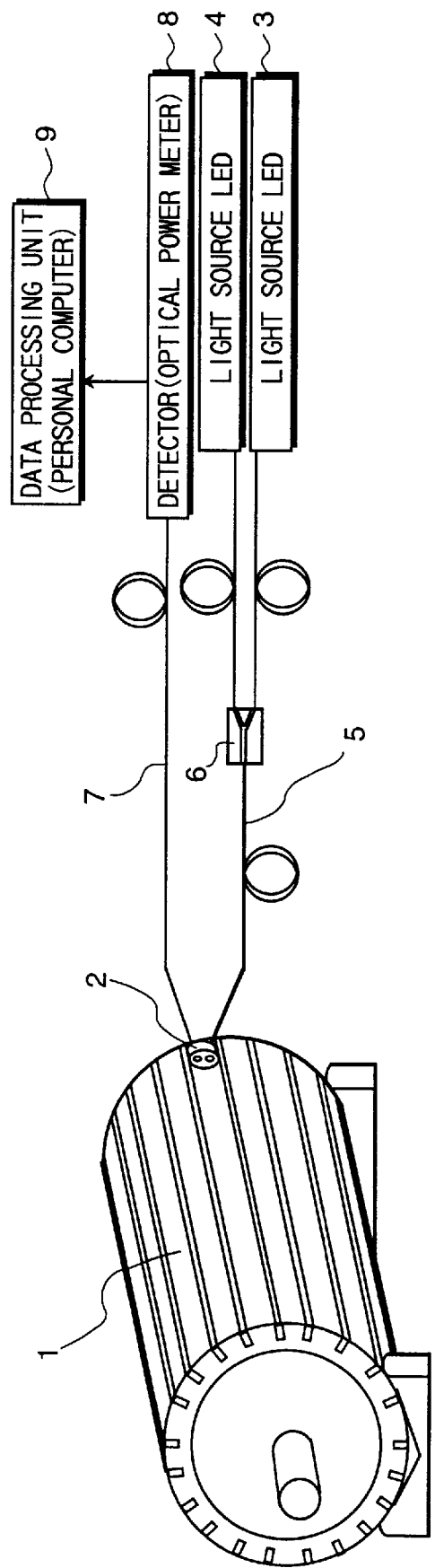
FIG. 1 is a diagram showing an example of a nondestructive diagnostic apparatus in conjunction with a rotor of a rotating machine according to a first embodiment.
Figure 2:
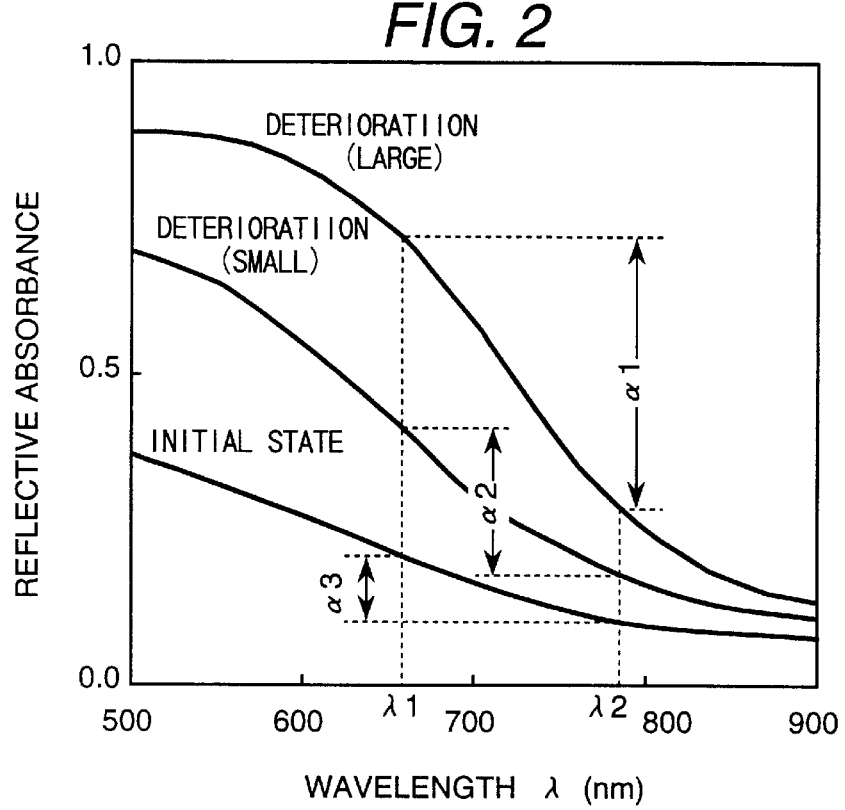
FIG. 2 is a graph showing an example of change in absorbance spectrum.

FIG. 1 shows an example of diagnosing the weight reduction ratio of an epoxy resin fixing a rotor bar by measuring light beams reflected from a surface of a rotor 1 of a rotating machine. First, the quantities of reference light at different wavelengths of two light source LEDs 3 and 4 are measured. In the embodiment, $l_1$ is set to 670 nm and $l_2$ is set to 1300 nm. For this purpose, a monochromatic light beam at the peak wavelength 1 generated from the light source LED 3 passes through an irradiation optical fiber 5 via an optical coupler 6 and is irradiated onto a standard white sheet from a probe 2. The invention is not especially limited to use of a standard white sheet. An alumina oxide surface, a white regular sheet, or the like can be also used. A chrome plated metal plate or the like can be also used without any problem. The reflected light beam is transferred to a detector (a photocell or an optical power meter) 8 via a light receiving optical fiber 7. A quantity $I_1$ of the reference light beam at the peak wavelength $l_1$ is measured and is stored into a data processing unit (personal computer) 9. A similar operation is performed by using a monochromatic light beam at the peak wavelength $l_2$ generated from the light source LED 4 and a quantity $I_2$ of the reference light beam at the peak wavelength $l_2$ is stored into the data processing unit (personal computer) 9.

Subsequently, the quantity of reflected light from the surface of the rotor 1 of the rotating machine is measured. In a manner similar to the measurement of the quantities of the reference light beams, the monochromatic light beams from the light source LEDs 3 and 4 are used and irradiated onto the surface of the rotor 1 of the rotating machine and quantities $I_1'$ and $I_2'$ of the reflected light beams are measured.

In the data processing unit (personal computer) 9, a reflectance $Rl_1$ ($=100 \times I_1'/I_1$) at $l_1$ and a reflectance $Rl_2$ ($=100 \times I_2'/I_2$) at $l_2$ are calculated and stored. Since the reflectance at each of the wavelengths $l_1$ and $l_2$ can be obtained as mentioned above, the reflective absorbance difference $DA_1$ ($=Al_1-Al_2$) (the difference in absorbance of the object to be measured) at the two wavelengths can be obtained in the data processing unit (personal computer) 9.

Figure 4:
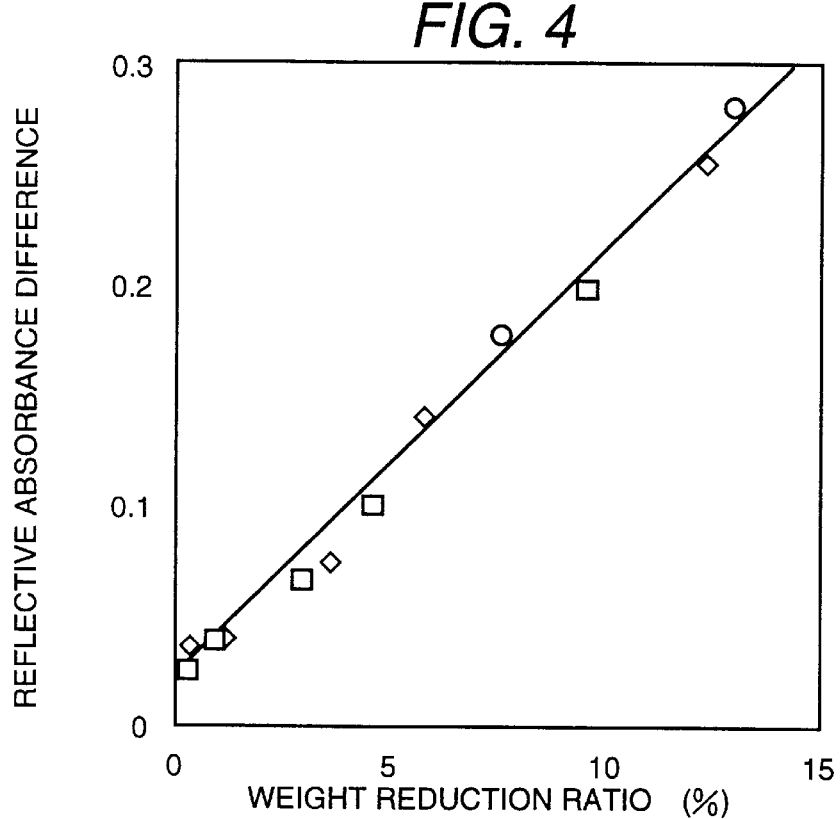
FIG. 4 is a graph showing an example of a diagnostic master curve showing the relation between a reflective absorbance difference and weight reduction ratio.

In the data processing unit (personal computer) 9, values of the difference in absorbance corresponding to the weight reduction ratio of the resin, as shown in FIG. 4, is preliminarily stored as a master curve, and the weight reduction ratio of the rotor 1 of the rotating machine is determined by comparing the stored values with the actually measured reflective absorbance difference $DA_1$, and the result is outputted as a measurement result to an external printer or the like (not shown).

Figure 5:
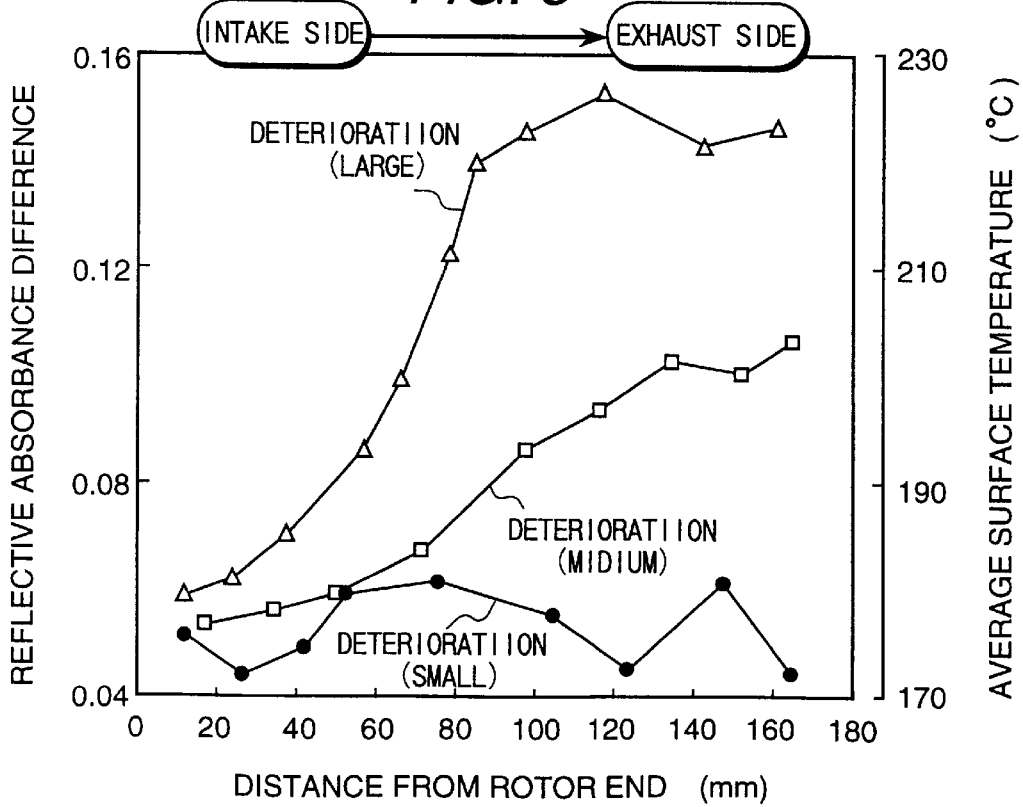
FIG. 5 is a graph showing an actual result of average surface temperature of the rotor of the rotating machine of the first embodiment and a reflective absorbance difference.

FIG. 5 shows results of continuously measuring the reflective absorbance difference from the intake side to the exhaust side of the rotor with respect to three rotors. Since the cooling efficiency on the exhaust side is lower, it is understood that the reflective absorbance difference on the exhaust side is larger in the rotor where deterioration is advanced. That is, it can be seen from FIG. 5 that the weight reduction ratio on the exhaust side is higher than that on the intake side.

Further, since an apparent activation energy LE of the epoxy resin used and the operating time (t) of each of the three rotating machines are known, the average surface temperature at the time of operation can be calculated by using the expression (4). The calculation result is shown in FIG. 5. As mentioned above, according to the invention, not only can the weight reduction ratio of the resin be estimated, but also the average operating temperature of the equipment which is increased during use, can be estimated.
(Second Embodiment)

Figure 6:
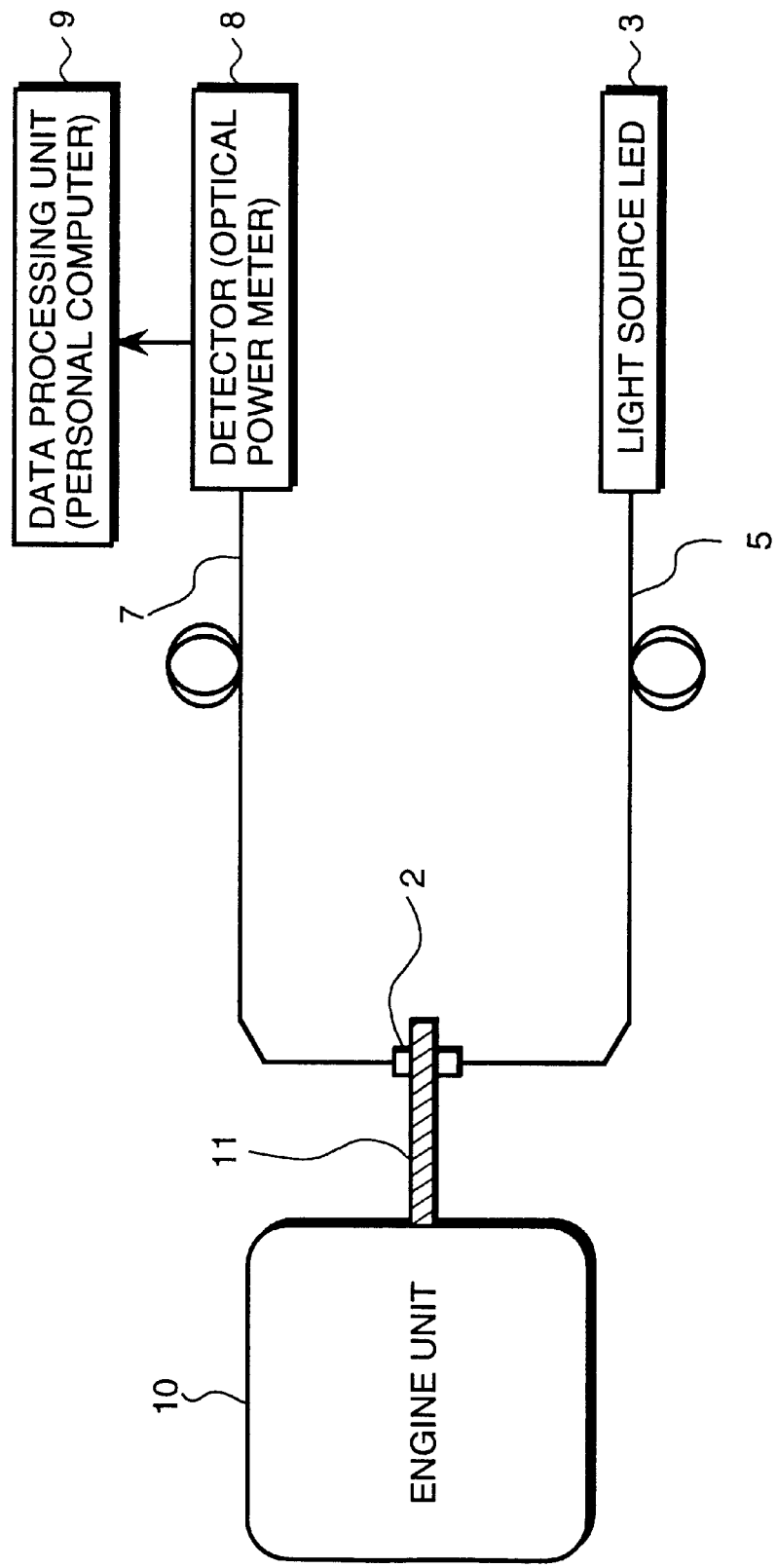
FIG. 6 is a diagram showing an example of a nondestructive diagnostic system as applied to a lubricating oil of an engine unit of a second embodiment.

FIG. 6 shows an example of nondestructively diagnosing the weight reduction ratio of a lubricating oil by measuring the quantity of a light beam transmitted to the lubricating oil of an engine unit 10 by using a flow cell 11.

First, a quantity of reference light from the light source LED 3 is measured in a manner similar to the first embodiment. In the second embodiment, $l_1$ is set to 850 nm. A monochromatic light beam at the peak wavelength $l_1$ generated from the light source LED 3 passes through the irradiation optical fiber 5 and is transferred to the light receiving optical fiber 7 via two probes 2, which are closely arranged so as to face each other. The transferred light beam is transmitted to the detector (optical power meter) 8, a quantity $I_1$ of the reference light beam at the peak wavelength $l_1$ is measured, and the result is stored into the data processing unit (personal computer) 9.

Subsequently, a quantity of a light transmitted to the lubricating oil of the engine unit 10 is measured. In a manner similar to the measurement of the reference light quantity, a quantity $I_1'$ of the light beam transmitted to the lubricating oil of the engine unit 10 is measured via the flow cell 11 having an optical path length (t) (mm, t=1 in the embodiment) interposed in a gap between the probes 2 arranged so as to face each other. In the data processing unit (personal computer) 9, the absorbance $A_1$ $(=-\log I_1'/I_1)$ at $l_1$ is calculated and stored.

Since the absorbance at the wavelength $l_1$ can be obtained as mentioned above, a light transmission loss $L_1$ (dB/mm) can be obtained according to the expression (3) in the data processing unit (personal computer) 9.

Figure 3:
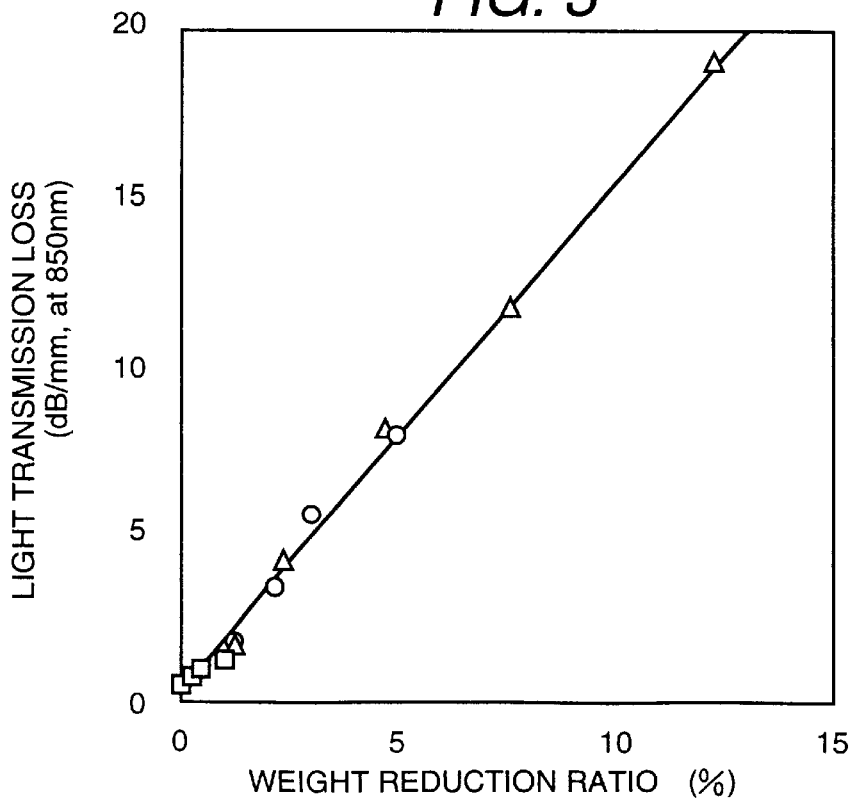
FIG. 3 is a graph showing an example of a diagnostic master curve showing the relation between light transmission loss and weight reduction ratio.

Values of a light transmission loss corresponding to the weight reduction ratio of the resin as shown in FIG. 3 have been preliminarily stored as a master curve in the data processing unit (personal computer) 9. The weight reduction ratio of the lubricating oil of the engine unit 10 is determined by comparing the stored values with the actually measured light transmission loss $L_1$ and the result is outputted as a measurement result to an external printer or the like (not shown).

According to the present invention, the weight reduction ratio of an insulating material, structural material, lubricating oil, or the like, which is used for equipment, can be nondestructively diagnosed without stopping the operation of the equipment.

What is claimed is:

1. A nondestructive diagnostic method for determining a weight reduction ratio of an object to be measured comprising the steps of:

directing irradiated light beams from light sources of at least two kinds of monochromatic light at different wavelengths and irradiating said light beams onto a surface of an object to be measured using an irradiation optical fiber;

leading reflected light beams from said surface of said object to be measured to a detector by using a light receiving optical fiber; and comparing a preliminarily stored value of weight reduction ratio of said object to be measured with a reflective absorbance difference at said different wavelengths so as to determine the present weight reduction ratio of said object to be measured in a data processing unit.

2. A nondestructive diagnostic method according to claim 1, wherein the object to be measured is an organic material object and the weight reduction ratio is determined substantially independent of thickness of the organic material object to be measured.

3. A nondestructive diagnostic method according to claim 2, wherein the organic material object to be measured is one of a resin and an oil.

4. A nondestructive diagnostic apparatus for determining a weight reduction ratio of an object to be measured comprising:

at least two kinds of monochromatic light sources supplying light at different wavelengths;

an irradiation optical fiber for irradiating said light beams from said light sources onto a surface of an object to be measured;

a light receiving optical fiber for receiving reflected light beams from said surface of said object to be measured and leading said light beams to a detector;

a detector for detecting the intensity of each of said reflected light beams at said different wavelengths and outputting measured values as electric signals; and a data processing unit for comparing a reflective absorbance at each wavelength with preliminarily stored values of weight reduction ratio of said object to be measured from an output value of said detector so as to determine the present weight reduction ratio of said object to be measured.

5. A nondestructive diagnostic apparatus according to claim 4, wherein the object to be measured is an organic material object and the weight reduction ratio is determined substantially independent of thickness of the organic material object to be measured.

6. A nondestructive diagnostic apparatus according to claim 5, wherein the organic material object to be measured is one of a resin and an oil.

7. A nondestructive diagnostic method for determining a weight reduction ratio of an organic material object to be measured, comprising the steps of:

irradiating at least two kinds of monochromatic light beams at different wavelengths onto a surface of an organic material object to be measured;

detecting a reflected light beam intensity from the surface of the organic material object to be measured at each wavelength;

determining a reflective absorbance difference at the different wavelengths from the detected reflected light beam intensity; and utilizing preliminarily stored values of a weight reduction ratio of the organic material object to be measured and the reflective absorbance difference at the different wavelengths so as to determine the present weight reduction ratio of the object to be measured.

8. A nondestructive diagnostic method according to claim 7, wherein at least one of the at least two kinds of monochromatic light beams is supplied onto the surface of the organic material object to be measured by a monochromatic light source having a peak wavelength of more than 660 nm but less than 1550 nm through an optical fiber.

9. A nondestructive diagnostic method according to claim 7, wherein the organic material object to be measured is one of a resin and an oil.

10. A nondestructive diagnostic apparatus for determining a weight reduction ratio of an organic material object to be measured, comprising:

at least two kinds of monochromatic light sources producing light at different wavelengths;

an irradiation optical fiber for irradiating the light beams from the light sources onto a surface of an organic material object to be measured;

a light receiving optical fiber for receiving reflected light beams from the surface of the organic material object to be measured;

a detector for receiving the reflected light beams from the light receiving optical fiber for detecting the intensity of each of the reflected light beams at the different wavelengths and for providing an output of measured values thereof as electric signals; and a data processing unit for calculating a reflective light absorbance at each wavelength based upon the electric signals from the detector, determining a reflective absorbance difference at the different wavelengths, and comparing preliminary stored values of the weight reduction ratio of the organic material object to be measured with the reflective absorbance difference at the different wavelengths so as to determine the present weight reduction ratio of the organic material object to be measured.

11. A nondestructive diagnostic apparatus according to claim 10, wherein the at least two kinds of monochromatic light sources include at least one of a LED light source and a LD light source, each having a peak wavelength of more than 660 nm but less than 1550 nm.

12. A nondestructive diagnostic apparatus according to claim 10, wherein the organic material object to be measured is one of a resin and an oil.

13. A nondestructive diagnostic method for determining a weight reduction ratio of an organic material object to be measured, comprising the steps of:

irradiating an illumination light beam from at least one kind of a monochromatic light source onto an organic material object to be measured;

detecting a transmitted light beam intensity from the organic material object to be measured;

determining a light transmission loss from the transmitted light beam intensity; and utilizing preliminary stored values of a weight reduction ratio of the organic material object to be measured and the determined light transmission loss to determine the present weight reduction ratio of the organic material object to be measured.

14. A nondestructive diagnostic method according to claim 13, wherein the at least one kind of monochromatic light source is a light source having a peak wavelength of more than 660 nm but less than 1550 nm.

15. A nondestructive diagnostic method according to claim 13, wherein the organic material object to be measured is one of a resin and an oil.

16. A nondestructive diagnostic apparatus for determining a weight reduction ratio of an organic material object to be measured, comprising:

a light source of at least one kind of monochromatic light beam;

an irradiation optical fiber for irradiating the light beam from the light source onto a surface of an organic material object to be measured;

a light receiving optical fiber which is arranged so as to face the irradiation optical fiber for receiving a transmitted light beam from the organic material object to be measured;

a detector for receiving the transmitted light beam from the light receiving optical fiber and for detecting the intensity of the transmitted light beam and for outputting a measured value thereof as an electric signal; and a data processing unit for determining a light transmission loss from an output value of the detector and for comparing preliminarily stored values of a weight reduction ratio of the organic material object to be measured with the determined light transmission loss so as to determine the present weight reduction ratio of the organic material object to be measured.

17. A nondestructive diagnostic apparatus according to claim 16, wherein the light source of at least one kind of monochromatic light beam includes one of a LED light source and a LD light source, each having a peak wavelength of more 660 nm but less than 1550 nm.

* * * * *